United States Patent [19]
Edmonds

[11] Patent Number: 6,159,750
[45] Date of Patent: *Dec. 12, 2000

[54] FLUORESCENCE POLARIZATION IMMUNOASSAY DIAGNOSTIC METHOD

[75] Inventor: Dan M. Edmonds, Grayslake, Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/959,543

[22] Filed: Oct. 24, 1997

Related U.S. Application Data

[63] Continuation of application No. 08/577,885, Dec. 22, 1995, abandoned.

[51] Int. Cl.[7] .................................................. G01N 33/542
[52] U.S. Cl. ............................................. 436/537; 436/805
[58] Field of Search ..................................... 436/536, 546, 436/537, 805, 172, 174; 435/4, 7.1

[56] References Cited

U.S. PATENT DOCUMENTS

| | | |
|---|---|---|
| 4,492,762 | 1/1985 | Wang et al. . |
| 4,585,862 | 4/1986 | Wang et al. . |
| 4,939,264 | 7/1990 | Heiman et al. . |
| 5,206,179 | 4/1993 | Ramsey . |
| 5,358,691 | 10/1994 | Clark et al. . |
| 5,391,740 | 2/1995 | Wang et al. . |
| 5,741,715 | 4/1998 | Ghoshal et al. ................... 436/537 |

FOREIGN PATENT DOCUMENTS 0240021   10/1987   European Pat. Off. .

OTHER PUBLICATIONS

M.T. Shipchandler et al., "Rapid, Fully Automated Measurement of Plasma Homocyst(e)ine with the Abbott IMx® Analyzer", *Clin Chem*, vol. 41, No. 7 (1995), pp. 991–994.

M.E. Jolley, et al., "Fluorescence Polarization Immunoasssy I. Monitoring Aminoglycoside Antibiotics in Serum and Plasma", *Clinical Chemistry*, vol. 27, No. 7, pp. 1189–1197 (1981).

Hicks et al (eds) "Laboratory Instrumentation" Third Edition J. P. Lippincott Company, Pennsylvania, USA, 1987.

*Primary Examiner*—David Saunders
*Attorney, Agent, or Firm*—Regina M. Anderson

[57] ABSTRACT

A method for fluorescence polarization immunoassay (FPIA) involves adding to a fluid container one or more reagents and a sample whose analyte is to be detected and measured, and then taking a first polarization measurement of the sample. More reagent is then added to the sample in the container, with no further sample addition to the container. A second or final polarization measurement of the sample is then taken, and the concentration of the analyte in the sample is then calculated based on the value of the two polarization measurements.

7 Claims, 3 Drawing Sheets

FLUORESCENCE POLARIZATION IMMUNOASSAY DIAGNOSTIC METHOD

This application is a File Wrapper Continuation of application Ser. No. 08/577,885, filed Dec. 22, 1995 and now abandoned.

FIELD OF THE INVENTION

The invention relates to immunoassay methods, and more particularly, to methods of fluorescence polarization immunoassays requiring only one addition to a fluid container of a sample containing analyte to be measured.

BACKGROUND

Fluorescence polarization immunoassay (FPIA) is a common method of analyzing liquid samples for the presence of an analyte of interest. As described in U.S. Pat. Nos. 5,391,740, 4,939,264, 4,585,862 and 4,492,762, the salient portions of which are incorporated herein by reference, as well as elsewhere, this technique generally consists of measuring the polarization characteristics of a diluted sample of the liquid mixed with a fluorophore and a binding substance that binds the fluorophore to the analyte of interest in an amount that is dependent on the concentration of that analyte.

It has long been recognized that some endogenous substances (bilirubin, for example) may interfere with FPIA measurements due to their inherent polarization characteristics. The conventional method for eliminating this interference is to measure the polarization characteristics of a "blank." That is, the polarization characteristics are measured for a mixture of sample, reagents and diluent, but without the fluorophore, at a sample dilution that is identical to the dilution of the sample mixture to be measured after incubation with the reagents (including the fluorophore and binding substance). The polarization characteristics of the "blank" are subtracted from the polarization characteristics of the actual sample, yielding the polarization level of the analyte/fluorophore mixture free of the interference of other constituents in the sample (Jolley et. al, *Clin Chem* 27 (7):1189–1197, 1981).

The measurement of a blank is easily executed in manual and small immunoassay systems. One method is to perform two analyses in two cuvettes, the difference being that one of the analyses is the blank and does not contain the fluorophore in its reagent mixture. A second method is to perform the two analyses sequentially. The sample and reagents (without the fluorophore) are mixed in a cuvette and the blank polarization characteristics are measured. Additional sample is then deposited in the cuvette along with additional reagents (maintaining the same sample dilution as in the blank measurement) and, following incubation, the final polarization characteristics are measured. In both of these methods, as in all current FPIA analysis systems, the dilution of the sample is the same in both the blank read and the final read of the polarization characteristics.

These methods of measuring blank polarization characteristics can be somewhat problematical for high-volume automated immunoassay systems, such as those performed on devices similar to that described in U.S. Pat. No. 5,358, 691, incorporated herein by reference. The first method requires two analysis cuvettes. With a system that processes cuvettes in an assembly-line fashion, this requirement effectively reduces the processing capacity of the system by fifty percent, since every other cuvette is used for blank measurement. The second method requires only one cuvette, but it requires two separate depositions of sample into that cuvette. Again, for an automated system that operates in an assembly-line fashion, this requirement excessively complicates system design and manufacture. The second addition of sample necessarily takes place at a later time than the first deposition, since the reading of the blank polarization characteristics must be interposed. In an assembly-line instrument, this difference in time means that the second deposition of sample must occur at a different location as well, so the sample must be transported or piped to two separate locations for deposition in the analysis cuvette. This dual sample access requirement increases instrument complexity and cost, reduces instrument reliability, and presents increased risk of sample spillage and instrument contamination. There is, therefore, great utility for a method of performing FPIA analytical tests that requires only a single sample access during the analytical process.

SUMMARY OF THE INVENTION

The present invention is directed to a method of performing a fluorescence polarization immunoassay (FPIA) using a single fluid container and a one time only sample addition. As that term is used herein, "single fluid container" refers to the container in which sample, plus any diluents and reagents are mixed prior to any polarization measurements.

In particular, a method of performing a fluorescence polarization immunoassay (FPIA) comprises making more than one fluorescence polarization measurement, preferably two, and using a single fluid container and a one time only sample addition.

In a preferred embodiment of the invention, there is a method of performing a fluorescence polarization immunoassay (FPIA) for the detection and/or measurement of concentration of an analyte, comprising the steps of:

a) adding one or more reagents and a sample to be analyzed to a fluid container;

b) taking a first polarization measurement of said sample;

c) adding more reagent to said sample in said container, with no further sample addition to said container;

d) taking a second or final polarization measurement; and e) calculating the concentration of analyte in said sample based on the value of said two polarization measurements.

According to the method of the invention the sample containing the analyte is added to the fluid container along with one or more reagents in step a).

Prior to the first polarization measurement in step b), a quantity of sample and reagent is often removed from the fluid container by means known in the art, preferably by aspiration, and this quantity is then utilized for the first polarization measurement. It is especially desirable that the amount removed be equal to about ½ the sample mixture volume.

The addition of more reagent-in step c) is such that the resulting dilution of the sample is a fraction X of the dilution of the sample after step a). It is desirable that X will equal about ½, but any known and measurable fraction of dilution will be available and may be utilized by the skilled artisan. It should be noted here that "dilution" refers to the dilution of the sample containing the analyte of interest, and not to the concentration of the analyte itself, which as an unknown is to be ascertained and measured.

Once the desired dilution fraction X has been set forth, it will then be possible to determine the amount of reagent to be added to the fluid container in step c) prior to the second FPIA measurement. The amount of reagent to be added can be determined utilizing a formula, and variations thereof, hereinafter set forth. In a particularly preferred embodiment, the quantity of reagent added in step c) will be about equal to any amount that had been removed from the fluid container for measurement as per step b). Again, the dilution of sample after step c) should be a fraction X, preferably about ½, of the dilution of sample after step a). If necessary, additional diluent may be included in step c) along with the reagent such that the total quantity of diluent plus reagent added will be such as to achieve the desired dilution fraction X. It should again be noted that while additional reagent(s) and/or diluent(s) are added in step c), there is no further addition of sample to the fluid container. In other words, sample need only be added once to the fluid container, and this is done prior to the start of any measurements in step a).

The analyte concentration is most often calculated from the difference between the first and second polarization measurements, at least one of the measurements being adjusted to compensate for the difference in dilutions of the sample following step a) and step c) according to the dilution fraction X, hereinafter further set forth. Preferably in step e) the analyte concentration is determined from the difference between the first and second polarization measurements, the first polarization measurement having been adjusted by multiplying that measurement by the fraction X above.

DETAILED DESCRIPTION OF PREFERRED EMBODIMENTS

The invention generally relates to a method of performing analytical tests. More specifically, it relates to a method of performing fluorescence polarization immunoassays. In particular, it relates to a method of measuring a reference polarization value and a second polarization value and determining from these values the concentration of an analyte in a body fluid. A particular advantage of this method is that it requires only a single fluid container or cuvette and a single transfer of a sample of the body fluid to that cuvette. In the method according to the invention, there is no second addition of sample required, thereby increasing throughput and efficiency. The method according to the various embodiments can be suitably executed on an IMx® and TDx® automated immunoassay instruments (Abbott Labs, Abbott Park, Ill.), but should be particularly well adapted to even higher volume automated immunoassay systems.

As heretofore set forth, there is a method of performing a fluorescence polarization immunoassay (FPIA) for the detection and measurement of concentration of an analyte, comprising the steps of:

a) adding one or more reagents and a sample to be analyzed to a fluid container;

b) taking a first polarization measurement of said sample;

c) adding more reagent to said sample in said container, with no further sample addition to said container;

d) taking a second or final polarization measurement; and e) calculating the concentration of analyte in said sample based on the value of said two polarization measurements.

Figure 1:
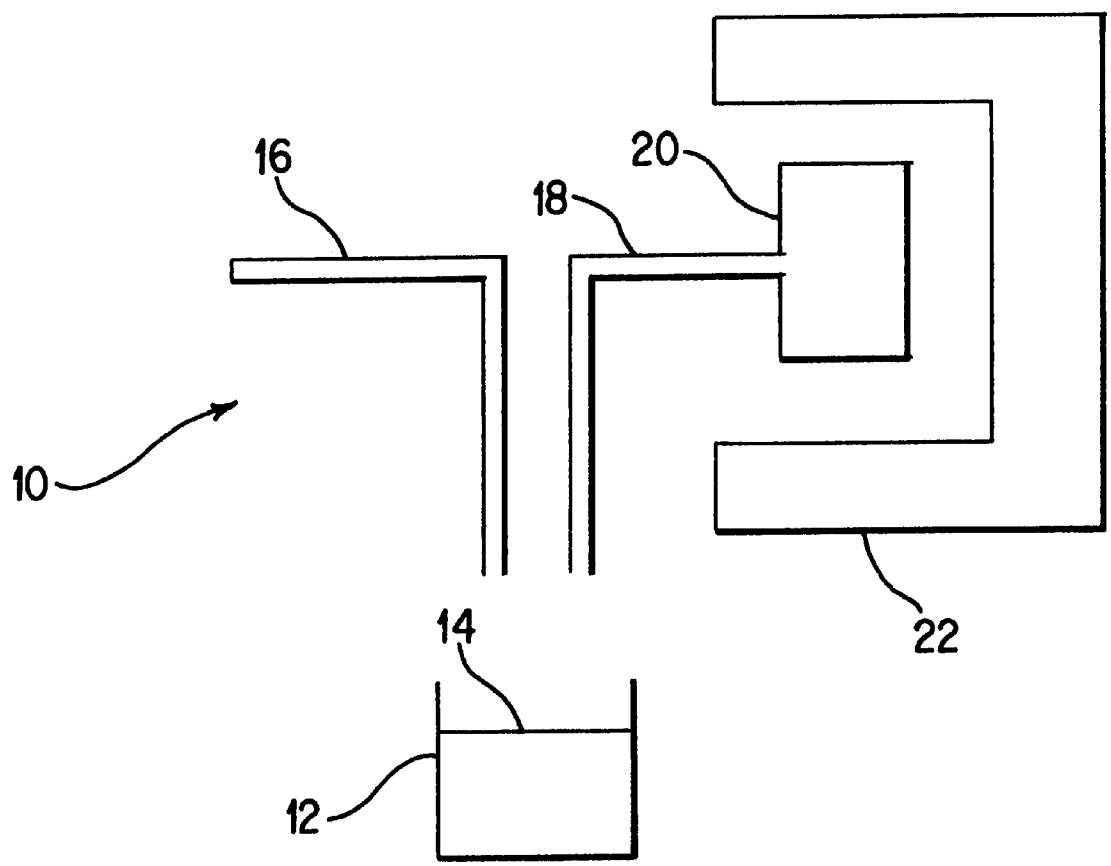
FIG. 1 is a schematic representation of an analytical cuvette and measuring apparatus as part of an automated immunoassay system.

Referring now to FIG. 1, there is illustrated the basic components of a device that may be utilized to execute the method of performing an analytical test according to the invention. An analytical device 10 comprises a fluid container 12, in which there is placed a sample to be analyzed 14. The fluid container may be any known to those skilled in the art and used for measurement, for example an analytical cuvette. A fluid dispensing device 16 is capable of dispensing a variety of liquids such as diluents or analytical reagents into the fluid container 12. A fluid aspiration device 18 is capable of removing fluid from the fluid container 12 and conveying it to a reading chamber 20. A polarization detection device 22 is deployed in the vicinity of the reading chamber 20.

The general method of analysis of embodiments of the invention includes the technique of fluorescence polarization immunoassay known to those skilled in the art, as described, for example, in various issued U.S. patents heretofore mentioned and elswhere. Reagents and diluents similar to those described in this reference and others available in the field may be used in embodiments of the present invention hereinafter set forth.

One embodiment of the method of the present invention may be described in conjunction with the operation of the device illustrated in FIG. 1. In step a) of the method, a sample 14 of a body fluid such as blood, serum, plasma, or urine, etc. is placed and contained in the fluid container 12. The volume or quantity of the sample 14 may be referred to as $V_S$. The fluid dispensing device 16 dispenses into the fluid container 12 a volume of a first reagent mixture into the fluid container 12, where it mixes with the sample 14. The volume dispensed by the fluid dispensing device 16 may be referred to as $V_1$. The first reagent mixture may contain mixtures of pretreatment reagent, antisera, and diluent widely available and known to those skilled in the art, and often dependent upon the analyte to be ascertained and measured. The dilution of the sample at this point may be defined as the sample volume $V_S$ divided by the total volume $V_S + V_1$ and termed $D_1$:

$$D_1 = \frac{V_S}{V_S + V_1} \quad (1)$$

For step b), the fluid aspiration device 18 then may remove, preferably by aspiration, a volume of the sample and reagent mixture and convey it to the readout chamber 20. The volume of the mixture aspirated may be referred to as $V_A$. The polarization detection device 22 reads the polarization characteristics of the mixture in the readout chamber 20, normally consisting of the vertical reference polarization ($V_{blank}$) and the horizontal reference polarization ($H_{blank}$). The vertical reference polarization $V_{blank}$ is the fluorescent light emitted with vertical polarization following excitation by light polarized vertically. The horizontal reference polarization $H_{blank}$ is the fluorescent light emitted with vertical polarization following excitation by light polarized horizontally. The readout chamber 20 is then emptied and flushed.

Alternately, the reference polarization measurement may be made within the fluid container 12, with no fluid aspirated and $V_A$ equal to zero. In either case, the dilution of the sample at this point is still equal to $D_1$, and the volume of sample remaining in the fluid container 12 is equal to $D_1(V_S+V_1-V_A)$.

For step c), the fluid dispensing device 16 then dispenses a volume of a second reagent mixture into the fluid container 12, where it mixes with the remaining sample 14 and first reagent mixture. The second reagent mixture may contain a fluorescent substance that will bind to the analyte of interest and a binding substance such as an antibody that will competitively bind to the analyte of interest. The volume of the second reagent mixture dispensed into the fluid container 12 may be referred to as $V_2$, and is selected so that the dilution of the sample in the mixture following dispensing of the second reagent mixture (termed $D_2$ and defined as the volume of sample remaining in the fluid container 12 following the aspiration divided by the total volume of fluid following the second reagent addition), is a specified fraction X (one half, for example, or one third, one quarter etc.) of the dilution of the sample in the mixture following dispensing the first reagent mixture therein:

$$D_2 = \frac{D_1(V_s + V_1 - V_A)}{V_S + V_1 - V_A + V_2} \quad (2)$$

$$= XD_1$$

therefore $$X = \frac{(V_s + V_1 - V_A)}{V_S + V_1 - V_A + V_2}$$

To achieve a desired value of X, the ratio of dilution following the second reagent addition divided by the dilution following the first reagent addition, the volume $V_2$ should therefore equal:

$$V_2 = \left(\frac{1}{X} - 1\right)(V_S + V_1 - V_A) \quad (3)$$

As an example, to achieve a dilution of one half of the initial dilution (X equals ½), the value of $V_2$ is:

$$V_2 = V_1 + V_S - V_A \quad (4)$$

In a particularly preferred embodiment, the aspiration volume equals half of the sample volume plus the first reagent volume:

$$V_A = \tfrac{1}{2}(V_S + V_1) \quad (5)$$

so the second dispense volume $V_2$ is equal to $V_A$.

In a different embodiment, the sample dilution following the second reagent addition is two-thirds of the sample dilution following the first reagent addition (X=⅔). To achieve this state, the value of $V_2$ or amount of reagent to be added in step c) is:

$$V_2 \tfrac{1}{2}(V_1 + V_S - V_A) \quad (6)$$

In this second case, if the aspiration volume equals half of the sample volume plus the first reagent volume, as in equation (5), the second dispense volume is equal to one half of $V_A$. Those skilled in the art will find that other formulas for $V_2$ may be readily ascertained by simply determining the dilution, or value of X, one desires.

For step d), a period of time is allowed to pass for incubation, after which the aspiration device 18 withdraws a volume of the mixture and conveys it to the readout chamber 20. The polarization detection device 22 reads the polarization characteristics of the mixture in the readout chamber 20, normally consisting of the vertical polarization ($V_{final}$) and the horizontal polarization ($H_{final}$). As with the reference polarizations, the vertical polarization $V_{blank}$ is the fluorescent light emitted with vertical polarization following excitation by light polarized vertically, and the horizontal polarization $H_{final}$ is the fluorescent light emitted with vertical polarization following excitation by light polarized horizontally. Alternatively as in step b), the final polarization characteristics of the sample mixture may be made within the fluid container with no fluid aspiration or removal.

For step e), the overall polarization characteristics of the sample in this analysis, which is a reproducible function of the concentration of the analyte of interest, are calculated in arbitrary units of mP. The polarization is calculated after adjusting the reference polarization values by the fraction equal to the ratio of the second sample dilution to the first sample dilution. In the case that the second sample dilution was one half of the first sample dilution (X=½ as described above):

$$V = V_{final} - \frac{V_{blank}}{2} \quad (7)$$

$$H = H_{final} - \frac{H_{blank}}{2}$$

$$\text{polarization} = \frac{V - H}{V + H} \times 1000 \; mP$$

If the dilution between the first and second samples had been ⅔, such that X=⅔ then this value would be substituted for the ½ in the above formula. As previously set forth, the above calculations may be modified according to any value of X, or dilution fraction, which the skilled artisan may wish to utilize.

In performing some analytical tests, it may be preferable to predilute the sample 14 prior to any reagent additions. In such a case, the sample 14 may be prediluted by dispensing diluent into the fluid container 12 to mix with and dilute the sample. Diluent may be added in quantities of about 10 to 1000 times the volume of the sample, more preferably about 15 to 300 times, and especially preferable about 20 to 250 times. A portion of the prediluted sample may then be removed from the container and discarded. The volume of prediluted sample remaining in the fluid container 12 is considered $V_S$, and the further dilutions resulting from reagent additions are calculated and controlled as discussed above. Those skilled in the art will further recognize that the initial polarization measurement may also be made within the fluid container itself, without withdrawing any sample therefrom. In this instance, the calculations hereinafter set forth will be adjusted (as described) to reflect the fact that no volume of sample is removed from the fluid container prior to the first polarization measurement.

It is envisioned that the method of the invention may be adapted to all especially high volume immunoassay measurement systems. It is also within the scope of the invention that the method of analysis herein set forth be adaptable to and utilized in all systems for detecting and measuring analytes wherein it is highly desirable to have only one addition of sample to the fluid container.

The following examples illustrate various embodiments of the invention, but should not be construed as limiting the scope thereof.

EXAMPLES

Example 1
Detection and Measurement of Amikacin

An embodiment of the invention was used to measure the concentration of Amikacin in a series of fluid samples of known Amikacin concentration. The analysis used TDx® Amikacin chemical regents (termed "T-Pot," "P-Pot," "S-Pot," and diluent) available from Abbott Laboratories, Abbott Park, Ill. and was performed in a modified IMx® analytical instrument (also available from Abbott Laboratories).

1. 5 µl of sample was aspirated from a sample tube and dispensed into a cuvette, along with 795 µl of diluent.
2. 646 µl of the sample/diluent mixture was aspirated from the cuvette and dispensed into a waste container.
3. 20 µl of P-Pot and 626 µl of diluent were dispensed into the cuvette.
4. The mixture in the cuvette was incubated for 5 minutes at 34.0° C.
5. 400 µl of the mixture in the cuvette (the blank) was aspirated into an optical flowcell, in which its optical properties ($H_{blank}$ and $V_{blank}$) are measured.
6. 15 µl of T-Pot, 13 µl of S-Pot, and 372 µl of diluent were then added to the cuvette.
7. The mixture in the cuvette was incubated for 3.8 minutes at 34.0° C.
8. 400 µl of the mixture was aspirated into the optical flowcell, in which its optical properties ($H_{final}$ and $V_{final}$) were measured.
9. The polarization was calculated as described in equation (7).

Figure 2:
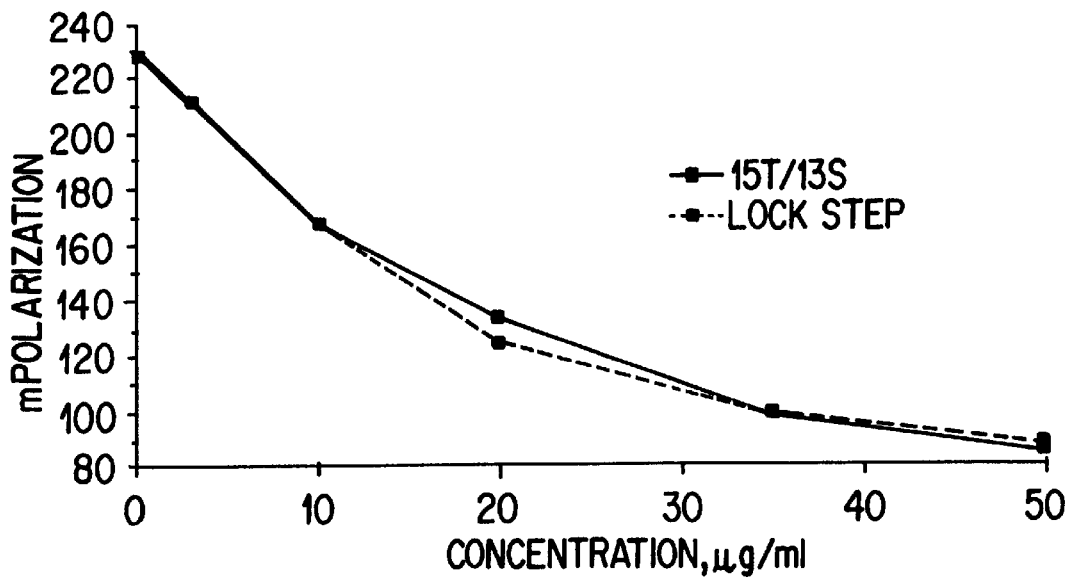
FIG. 2 is a graph showing FPIA measurement of Amikacin concentration according to one method of the invention in comparison to conventional FPIA measurements.

The results of these measurements are presented in FIG. 2, in comparison with FPIA measurements made with conventional sample addition and blank correction techniques. The effectiveness of this method in enabling accurate measurement of Amikacin is evident.

Example 2
Detection and measurement of T4

An embodiment of the process of the invention was used to measure the concentration of the hormone T4 in a series of fluid samples of known T4 concentration. In the analysis there was used TDx® T4 chemical regents (termed "T-Pot," "P-Pot," "S-Pot," and diluent) available from Abbott Laboratories, Abbott Park, Ill. and the analysis was performed in a modified IMx® analytical instrument (also available from Abbott Laboratories).

1. 14 µl of S-Pot, 25 µl of P-Pot, and 7 µl of sample were dispensed into the cuvette along with 747 µl of diluent.
2. The mixture in the cuvette was incubated for 5 minutes at 34.0° C.
3. 400 µl (µl) of the mixture in the cuvette (the blank) was aspirated into an optical flowcell, in which its optical properties ($H_{blank}$ and $V_{blank}$) were measured.
4. 10 µl of T-Pot and 390 µl of diluent were added to the cuvette.
5. The mixture in the cuvette was incubated for 3.8 minutes at 34.0° C.
6. 400 µl of the mixture was aspirated into the optical flowcell, in which its optical properties ($H_{final}$ and $V_{final}$) were measured.
7. The polarization was calculated as described in equation (7).

Figure 3:
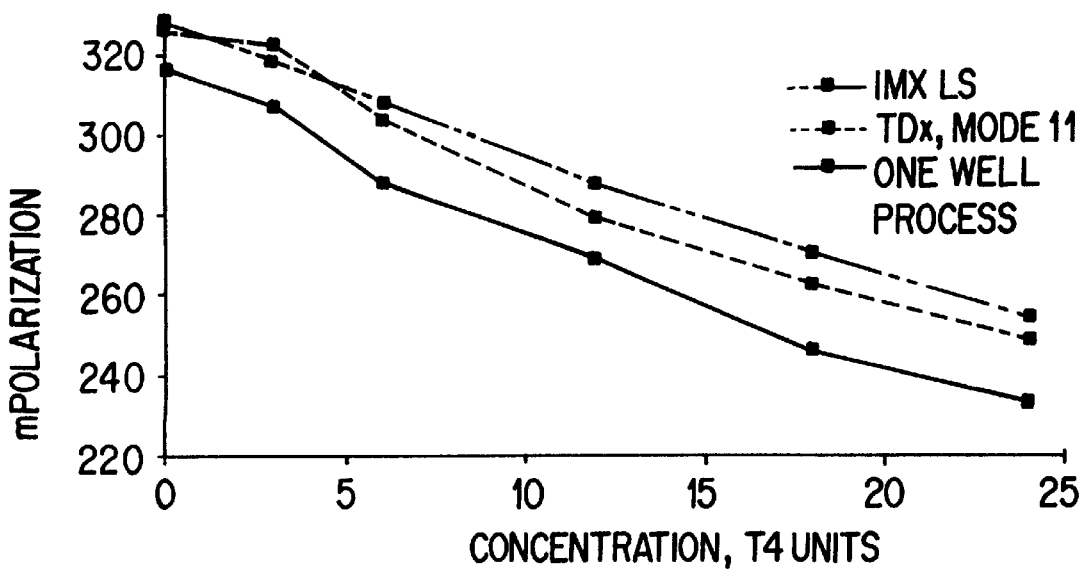
FIG. 3 is a graph showing FPIA measurement of T4 concentration according to one method of the invention in comparison to conventional FPIA measurements.

The results of these measurements were presented in FIG. 3, in comparison with FPIA measurements made with conventional sample addition and blank correction techniques. Although the curves are not identical, the variation in polarization span as a function of the T4 concentration is similar to that of the conventional technique, indicating the effectiveness of this method in enabling accurate measurement of T4.

Example 3
Detection and Measurement of Cannabinoids

An embodiment of the process of the invention was used to measure the concentration of cannabinoids in a series of fluid samples of known cannabinoid concentration. The analysis used TDx® cannabinoid chemical regents (termed "T-Pot," "W-Pot," "P-Pot," and "S-Pot,") available from Abbott Laboratories, Abbott Park, Ill. and was performed in a modified IMx® analytical instrument (also available from Abbott Laboratories).

1. 18 µl of sample, 11 µl of P-Pot, and 22 µl of S-Pot were dispensed into the cuvette along with 749 µl of W-pot.
2. The mixture in the cuvette was incubated for 5 minutes at 34.0° C.
3. 400 µl of the mixture in the cuvette (the blank) was aspirated into an optical flowcell, in which its optical properties ($H_{blank}$ and $V_{blank}$) were measured.
4. 11 µl of T-Pot, 6 µl of P-Pot, 11 µl of S-Pot and 372 µl of W-Pot were added to the cuvette.
5. The mixture in the cuvette was incubated for 3.8 minutes at 34.0° C.
6. 400 µl of the mixture was aspirated into the optical flowcell, in which its optical properties ($H_{final}$ and $V_{final}$) were measured.
7. The polarization was calculated as described in equation (7).

Figure 4:
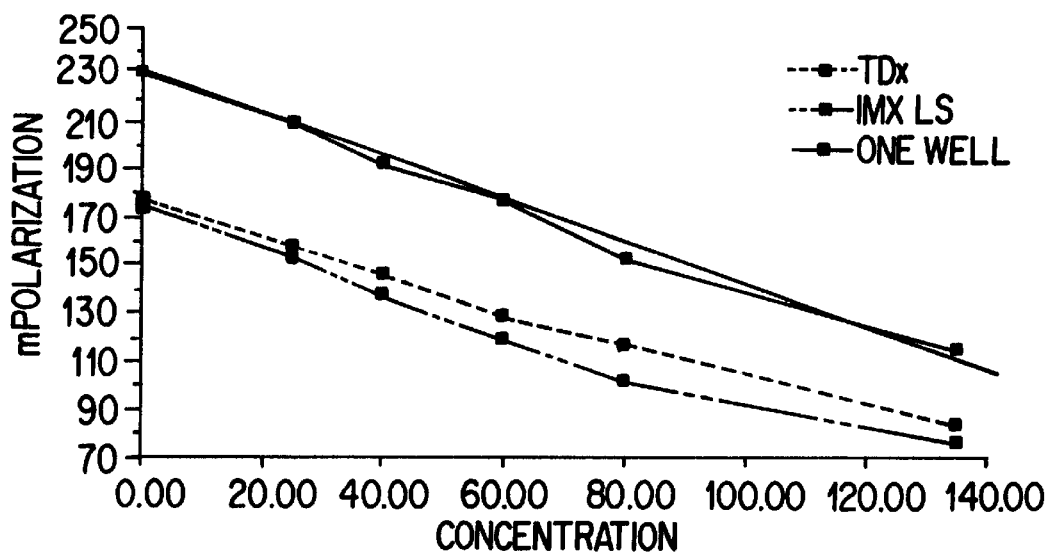
FIG. 4 is a graph showing FPIA measurement of cannabinoids concentration according to one method of the invention in comparison to conventional FPIA measurements.

The results of these measurements are presented in FIG. 4, in comparison with two sets of FPIA measurements made with conventional sample addition and blank correction techniques. Although the curves are not identical, the variation in polarization span as a function of the cannabinoid concentration is similar to that of the conventional technique, indicating the effectiveness of this method in enabling accurate measurement of cannabinoids.

Example 4
Detection and measurement of Free Estriol

An embodiment of the process of the invention was used to measure the free concentration of the hormone estriol in a series of fluid samples of known free estriol concentration. The analysis used TDx® free estriol chemical regents (termed "T-Pot," "P-Pot," "S-Pot," and diluent) available from Abbott Laboratories, Abbott Park, Ill. and was performed in a modified IMx® analytical instrument (also available from Abbott Laboratories).

1. 10 µ of S-Pot, 14 µl of P-Pot, and 34 µl of sample were dispensed into the cuvette along with 742 µl of diluent.
2. The mixture in the cuvette was incubated for 5 minutes at 34.0° C.
3. 400 µl of the mixture in the cuvette (the blank) was aspirated into an optical flowcell, in which its optical properties ($H_{blank}$ and $V_{blank}$) were measured.
4. 10 µl of T-Pot and 390 µl of diluent were added to the cuvette.
5. The mixture in the cuvette was incubated for 3.8 minutes at 34.0° C.

6. 400 µl of the mixture was aspirated into the optical flowcell, in which its optical properties ($H_{final}$ and $V_{final}$) were measured.

7. The polarization was calculated as described in equation (7).

Figure 5:
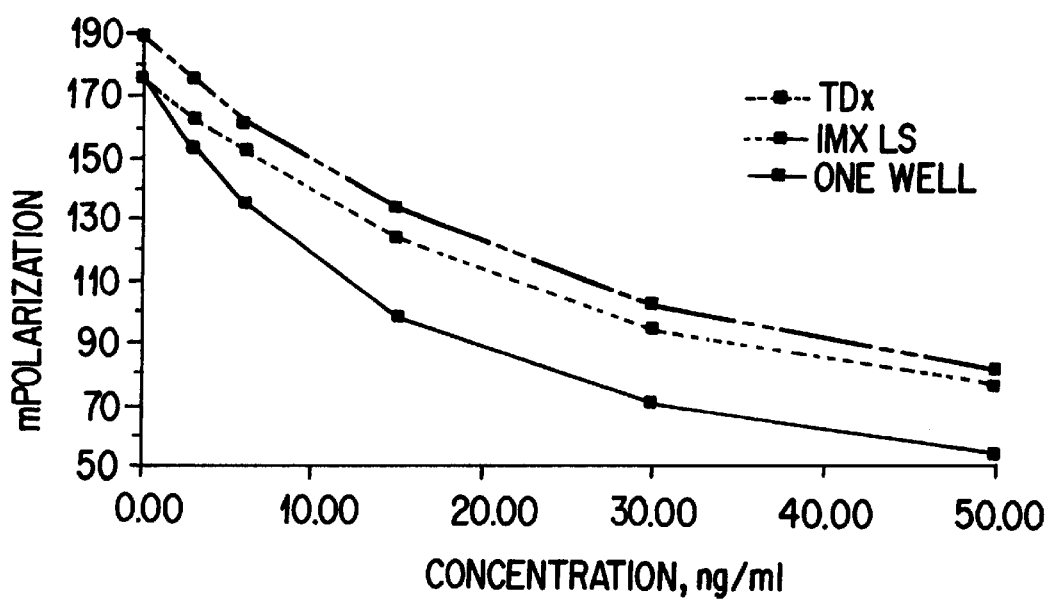
FIG. 5 is a graph showing FPIA measurement of free estriol concentration according to one method of the invention in comparison to conventional FPIA measurements.

The results of these measurements are presented in FIG. 5, in comparison with two sets of FPIA measurements made with conventional sample addition and blank correction techniques. Although the curves are not identical, the variation in polarization span as a function of the free estriol concentration is similar to that of the conventional technique, indicating the effectiveness of this method in enabling accurate measurement of free estriol.

While the invention has been described in each of its various embodiments, it is anticipated that those skilled in the art may conceive of and implement various modifications thereto, without departing from the true spirit and scope of the invention, as set forth in the specification and the accompanying claims.

What is claimed is:

1. A method of performing a fluorescence polarization immunoassay (FPIA) for the detection and quantification of an analyte's concentration, the method comprising the steps of:

a) adding one or more reagents and a sample to be analyzed to a fluid container, wherein at least one of the reagents is a diluent and the sample is at a specified dilution after the addition of the reagents;

b) removing a quantity of sample and reagent from said container;

c) taking a first polarization measurement of the sample;

d) adding one or more reagents to the sample in the container, with no further sample addition to the container, wherein at least one of the reagents is different from the reagents added in step a) and the addition of the reagents is such that a resulting dilution of the sample is a fraction X of the dilution of the sample after step a);

e) taking a second polarization measurement; and f) calculating the analyte's concentration in the sample by calculating the difference between the first and second polarization measurements, wherein at least one of the measurements is adjusted to compensate for the difference in the dilutions of the sample following step a) and step c).

2. The method of claim 1 wherein in step f) the first polarization measurement is adjusted by multiplying the measurement by the fraction X.

3. The method of claim 1 in which the measurement taken in step c) is performed on the quantity of sample and reagent removed from said container.

4. The method of claim 3 wherein said quantity of sample and reagent which is removed is equal to about one half the volume of said sample and reagent within a cuvette, said removed quantity being aspirated from said cuvette.

5. The method of claim 1 wherein in step d) said addition of reagents results in a sample dilution which is equal to about one half that of the dilution after step a) such that X equals about ½.

6. The method of claim 5, wherein in step d), additional diluent is added to the sample in said container with the reagents added in step d) such that the volume of the added diluent and added reagent is such that the dilution of the sample is equal to about one half that after step a) such that X equals about ½.

7. The method of claim 1, wherein in step d), additional diluent is added to the sample in the container with the reagents added in step d), wherein the added quantity of diluent is equal to the amount of the sample, diluent and reagents which have been removed.

* * * * *